United States Patent
Yablonski

(10) Patent No.: US 8,945,038 B2
(45) Date of Patent: *Feb. 3, 2015

(54) INTERNAL SHUNT AND METHOD FOR TREATING GLAUCOMA

(71) Applicant: Transcend Medical, Inc., Menlo Park, CA (US)

(72) Inventor: Michael Yablonski, Menlo Park, CA (US)

(73) Assignee: Transcend Medical, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/897,313

(22) Filed: May 17, 2013

(65) Prior Publication Data

US 2013/0253407 A1 Sep. 26, 2013

Related U.S. Application Data

(63) Continuation of application No. 12/711,201, filed on Feb. 23, 2010, now Pat. No. 8,444,588, which is a continuation of application No. 11/509,327, filed on Aug. 23, 2006, now abandoned, which is a continuation of application No. 10/429,336, filed on May 5, 2003, now abandoned.

(51) Int. Cl.
*A61M 5/00* (2006.01)
*A61F 9/007* (2006.01)
*A61F 9/00* (2006.01)

(52) U.S. Cl.
CPC .................................. *A61F 9/00781* (2013.01)
USPC .................... 604/8; 604/5.04; 604/9; 604/10; 604/19; 604/27; 604/28; 604/48; 604/93.01; 604/540; 604/541; 604/284; 604/285; 604/286; 604/288; 604/289; 604/290

(58) Field of Classification Search
USPC .............. 604/5.04, 8–10; 427/2.1, 2.24, 2.25; 600/398, 399
See application file for complete search history.

(56) References Cited

U.S. PATENT DOCUMENTS

| 2,990,670 A | 7/1961 | Kingsbury |
| 3,439,675 A | 4/1969 | Cohen |

(Continued)

FOREIGN PATENT DOCUMENTS

| EP | 0 228 185 A1 | 7/1987 |
| EP | 1184010 A2 | 3/2002 |

(Continued)

OTHER PUBLICATIONS

Barsky et al. "Evaluation of absorbable gelatin film (Gelfilm) in cyclodialysis clefts" Arch. Ophth. 60(6): 1044-1052,1958.

(Continued)

*Primary Examiner* — Tatyana Zalukaeva
*Assistant Examiner* — Ilya Treyger
(74) *Attorney, Agent, or Firm* — Fred C. Hernandez; Mintz Levin Cohn Ferris Glovsky and Popeo, P.C.

(57) ABSTRACT

A surgical technique and device wherein an indwelling tube is placed in the eye of a patient having glaucoma. The tube diverts aqueous humor from the anterior chamber to the suprachoroidal space from which it is removed by blood flowing in the choroidal and uveal tissues. This decreases the intraocular pressure.

15 Claims, 4 Drawing Sheets

(56) References Cited

U.S. PATENT DOCUMENTS

| | | |
|---|---|---|
| 3,767,759 A | 10/1973 | Wichterle |
| 3,788,327 A | 1/1974 | Donowitz et al. |
| 3,915,172 A | 10/1975 | Wichterle et al. |
| 4,037,604 A | 7/1977 | Newkirk |
| 4,402,681 A | 9/1983 | Haas et al. |
| 4,457,757 A | 7/1984 | Molteno |
| 4,521,210 A | 6/1985 | Wong |
| 4,554,918 A | 11/1985 | White |
| 4,604,087 A | 8/1986 | Joseph |
| 4,617,715 A | 10/1986 | Koistinen et al. |
| 4,634,418 A | 1/1987 | Binder |
| 4,722,724 A | 2/1988 | Schocket |
| 4,750,901 A | 6/1988 | Molteno |
| 4,787,885 A | 11/1988 | Binder |
| 4,826,478 A | 5/1989 | Schocket |
| 4,846,172 A | 7/1989 | Berlin |
| 4,863,457 A | 9/1989 | Lee |
| 4,886,488 A | 12/1989 | White |
| 4,900,300 A | 2/1990 | Lee |
| 4,946,436 A | 8/1990 | Smith |
| 4,968,296 A | 11/1990 | Ritch et al. |
| 5,041,081 A | 8/1991 | Odrich |
| 5,071,408 A | 12/1991 | Ahmed |
| 5,073,163 A | 12/1991 | Lippman |
| 5,092,837 A | 3/1992 | Ritch et al. |
| 5,127,901 A | 7/1992 | Odrich |
| 5,171,213 A | 12/1992 | Price, Jr. |
| 5,178,604 A | 1/1993 | Baerveldt et al. |
| 5,180,362 A | 1/1993 | Worst |
| 5,284,476 A | 2/1994 | Koch |
| 5,300,020 A | 4/1994 | L'Esperance, Jr. |
| 5,338,291 A | 8/1994 | Speckman et al. |
| 5,342,370 A | 8/1994 | Simon et al. |
| 5,346,464 A | 9/1994 | Camras |
| 5,370,607 A | 12/1994 | Memmen |
| 5,372,577 A | 12/1994 | Ungerleider |
| 5,397,300 A | 3/1995 | Baerveldt et al. |
| 5,433,701 A | 7/1995 | Rubinstein |
| 5,443,505 A | 8/1995 | Wong et al. |
| 5,454,746 A | 10/1995 | Guegan et al. |
| 5,476,445 A | 12/1995 | Baerveldt et al. |
| 5,558,629 A | 9/1996 | Baerveldt et al. |
| 5,558,630 A | 9/1996 | Fisher |
| RE35,390 E | 12/1996 | Smith |
| 5,601,094 A | 2/1997 | Reiss |
| 5,626,558 A | 5/1997 | Suson |
| 5,626,559 A | 5/1997 | Solomon |
| 5,651,782 A | 7/1997 | Simon et al. |
| 5,676,944 A | 10/1997 | Alvarado et al. |
| 5,702,414 A | 12/1997 | Richter et al. |
| 5,704,907 A | 1/1998 | Nordquist et al. |
| 5,713,844 A | 2/1998 | Peyman |
| 5,741,292 A | 4/1998 | Mendius |
| 5,743,868 A | 4/1998 | Brown et al. |
| 5,752,928 A | 5/1998 | de Roulhac et al. |
| 5,792,075 A | 8/1998 | Schwager |
| 5,807,244 A | 9/1998 | Barot |
| 5,807,302 A | 9/1998 | Wandel |
| 5,868,697 A | 2/1999 | Richter et al. |
| 5,882,327 A | 3/1999 | Jacob |
| 5,893,837 A | 4/1999 | Eagles et al. |
| 5,941,250 A | 8/1999 | Aramant et al. |
| 5,968,058 A | 10/1999 | Richter et al. |
| 6,007,510 A | 12/1999 | Nigam |
| 6,007,511 A | 12/1999 | Prywes |
| 6,019,786 A | 2/2000 | Thompson |
| 6,036,678 A | 3/2000 | Giungo |
| 6,050,970 A | 4/2000 | Baerveldt |
| 6,050,999 A | 4/2000 | Paraschac et al. |
| 6,077,299 A | 6/2000 | Adelberg et al. |
| 6,102,045 A | 8/2000 | Nordquist et al. |
| 6,142,969 A | 11/2000 | Nigam |
| 6,186,974 B1 | 2/2001 | Allan et al. |
| 6,203,513 B1 | 3/2001 | Yaron et al. |
| 6,221,078 B1 | 4/2001 | Bylsma |
| 6,251,090 B1 | 6/2001 | Avery et al. |
| 6,261,256 B1 | 7/2001 | Ahmed |
| 6,264,668 B1 | 7/2001 | Prywes |
| 6,270,472 B1 | 8/2001 | Antaki et al. |
| 6,331,313 B1 | 12/2001 | Wong et al. |
| 6,375,642 B1 | 4/2002 | Grieshaber et al. |
| 6,383,219 B1 | 5/2002 | Telandro et al. |
| 6,450,984 B1 | 9/2002 | Lynch et al. |
| 6,464,724 B1 | 10/2002 | Lynch et al. |
| 6,468,283 B1 | 10/2002 | Richter et al. |
| 6,471,666 B1 | 10/2002 | Odrich |
| 6,471,777 B1 | 10/2002 | Kobayashi et al. |
| 6,494,857 B1 | 12/2002 | Neuhann |
| 6,508,779 B1 | 1/2003 | Suson |
| 6,510,600 B2 | 1/2003 | Yaron et al. |
| 6,524,275 B1 | 2/2003 | Lynch et al. |
| 6,533,768 B1 | 3/2003 | Hill |
| 6,537,568 B2 | 3/2003 | Olejnik et al. |
| 6,544,208 B2 | 4/2003 | Ethier et al. |
| 6,544,249 B1 | 4/2003 | Yu et al. |
| 6,558,342 B1 | 5/2003 | Yaron et al. |
| 6,561,974 B1 | 5/2003 | Grieshaber et al. |
| 6,579,256 B2 | 6/2003 | Hughes |
| 6,589,203 B1 | 7/2003 | Mitrev |
| 6,595,945 B2 | 7/2003 | Brown |
| 6,626,858 B2 | 9/2003 | Lynch et al. |
| 6,638,239 B1 | 10/2003 | Bergheim et al. |
| 6,648,283 B2 | 11/2003 | Chase et al. |
| 6,666,841 B2 | 12/2003 | Gharib et al. |
| 6,676,607 B2 | 1/2004 | de Juan, Jr. et al. |
| 6,699,210 B2 | 3/2004 | Williams et al. |
| 6,699,211 B2 | 3/2004 | Savage |
| 6,719,750 B2 | 4/2004 | Varner et al. |
| 6,726,664 B2 | 4/2004 | Yaron et al. |
| 6,726,676 B2 | 4/2004 | Stegmann et al. |
| 6,730,056 B1 | 5/2004 | Ghaem et al. |
| 6,736,791 B1 | 5/2004 | Tu et al. |
| 6,741,666 B1 | 5/2004 | Henry et al. |
| 6,780,164 B2 | 8/2004 | Bergheim et al. |
| 6,783,544 B2 | 8/2004 | Lynch et al. |
| 6,786,888 B1 | 9/2004 | Zadno-Azizi et al. |
| 6,827,699 B2 | 12/2004 | Lynch et al. |
| 6,827,700 B2 | 12/2004 | Lynch et al. |
| 6,881,197 B1 | 4/2005 | Nigam |
| 6,881,198 B2 | 4/2005 | Brown |
| 6,939,298 B2 | 9/2005 | Brown et al. |
| 6,955,656 B2 | 10/2005 | Bergheim et al. |
| 6,962,573 B1 | 11/2005 | Wilcox |
| 6,966,888 B2 | 11/2005 | Cullen et al. |
| 6,969,384 B2 | 11/2005 | de Juan, Jr. et al. |
| 6,981,958 B1 | 1/2006 | Gharib et al. |
| 6,989,007 B2 | 1/2006 | Shadduck |
| 7,041,077 B2 | 5/2006 | Shields |
| 7,090,681 B2 | 8/2006 | Weber et al. |
| 7,094,225 B2 | 8/2006 | Tu et al. |
| 7,135,009 B2 | 11/2006 | Tu et al. |
| 7,160,264 B2 | 1/2007 | Lisk, Jr. et al. |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,195,774 B2 | 3/2007 | Carvalho et al. |
| 7,207,965 B2 | 4/2007 | Simon |
| 7,220,238 B2 | 5/2007 | Lynch et al. |
| 7,273,475 B2 | 9/2007 | Tu et al. |
| 7,291,125 B2 | 11/2007 | Coroneo |
| 7,297,130 B2 | 11/2007 | Bergheim et al. |
| 7,331,984 B2 | 2/2008 | Tu et al. |
| 7,431,710 B2 | 10/2008 | Tu et al. |
| 7,488,303 B1 | 2/2009 | Haffner et al. |
| 7,857,782 B2 | 12/2010 | Tu et al. |
| 8,075,511 B2 | 12/2011 | Tu et al. |
| 2002/0013546 A1 | 1/2002 | Grieshaber et al. |
| 2002/0013572 A1 | 1/2002 | Berlin |
| 2002/0072673 A1 | 6/2002 | Yamamoto et al. |
| 2002/0087111 A1 | 7/2002 | Ethier et al. |
| 2002/0111608 A1 | 8/2002 | Baerveldt et al. |
| 2002/0128613 A1 | 9/2002 | Nakayama |
| 2002/0133168 A1 | 9/2002 | Smedley et al. |
| 2002/0143284 A1 | 10/2002 | Tu et al. |

(56) References Cited

U.S. PATENT DOCUMENTS

| | | |
|---|---|---|
| 2002/0177856 A1 | 11/2002 | Richter et al. |
| 2002/0193725 A1 | 12/2002 | Odrich |
| 2003/0028228 A1 | 2/2003 | Sand |
| 2003/0055372 A1 | 3/2003 | Lynch et al. |
| 2003/0060752 A1 | 3/2003 | Bergheim et al. |
| 2003/0097151 A1 | 5/2003 | Smedley et al. |
| 2003/0097171 A1 | 5/2003 | Elliott |
| 2003/0135149 A1 | 7/2003 | Cullen et al. |
| 2003/0181848 A1 | 9/2003 | Bergheim et al. |
| 2003/0187384 A1 | 10/2003 | Bergheim et al. |
| 2003/0208163 A1 | 11/2003 | Yaron et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0015140 A1 | 1/2004 | Shields |
| 2004/0024345 A1 | 2/2004 | Gharib et al. |
| 2004/0050392 A1 | 3/2004 | Tu et al. |
| 2004/0073156 A1 | 4/2004 | Brown |
| 2004/0088048 A1 | 5/2004 | Richter et al. |
| 2004/0092856 A1 | 5/2004 | Dahan |
| 2004/0097984 A1 | 5/2004 | Zapata |
| 2004/0102729 A1 | 5/2004 | Haffner et al. |
| 2004/0111050 A1 | 6/2004 | Smedley et al. |
| 2004/0127843 A1 | 7/2004 | Tu et al. |
| 2004/0147870 A1 | 7/2004 | Burns et al. |
| 2004/0148022 A1 | 7/2004 | Eggleston |
| 2004/0193095 A1 | 9/2004 | Shadduck |
| 2004/0193262 A1 | 9/2004 | Shadduck |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225250 A1 | 11/2004 | Yablonski |
| 2004/0236343 A1 | 11/2004 | Taylor et al. |
| 2004/0249333 A1 | 12/2004 | Bergheim et al. |
| 2004/0254517 A1 | 12/2004 | Quiroz-Mercado et al. |
| 2004/0254519 A1 | 12/2004 | Tu et al. |
| 2004/0254520 A1 | 12/2004 | Porteous et al. |
| 2004/0254521 A1 | 12/2004 | Simon |
| 2004/0260228 A1 | 12/2004 | Lynch et al. |
| 2005/0008673 A1 | 1/2005 | Snyder et al. |
| 2005/0049578 A1 | 3/2005 | Tu et al. |
| 2005/0090806 A1 | 4/2005 | Lynch et al. |
| 2005/0090807 A1 | 4/2005 | Lynch et al. |
| 2005/0107734 A1 | 5/2005 | Coroneo |
| 2005/0119601 A9 | 6/2005 | Lynch et al. |
| 2005/0119636 A1 | 6/2005 | Haffner et al. |
| 2005/0119737 A1 | 6/2005 | Bene et al. |
| 2005/0125003 A1 | 6/2005 | Pinchuk et al. |
| 2005/0143817 A1 | 6/2005 | Hunter et al. |
| 2005/0149080 A1 | 7/2005 | Hunter et al. |
| 2005/0175663 A1 | 8/2005 | Hunter et al. |
| 2005/0181011 A1 | 8/2005 | Hunter et al. |
| 2005/0181977 A1 | 8/2005 | Hunter et al. |
| 2005/0182350 A1 | 8/2005 | Nigam |
| 2005/0191331 A1 | 9/2005 | Hunter et al. |
| 2005/0192527 A1 | 9/2005 | Gharib et al. |
| 2005/0197613 A1 | 9/2005 | Sniegowski et al. |
| 2005/0209549 A1 | 9/2005 | Bergheim et al. |
| 2005/0209550 A1 | 9/2005 | Bergheim et al. |
| 2005/0232972 A1 | 10/2005 | Odrich |
| 2005/0244462 A1 | 11/2005 | Farooq |
| 2005/0250788 A1 | 11/2005 | Tu et al. |
| 2005/0266047 A1 | 12/2005 | Tu et al. |
| 2005/0267397 A1 | 12/2005 | Bhalla |
| 2005/0267398 A1 | 12/2005 | Protopsaltis et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0283108 A1 | 12/2005 | Savage |
| 2005/0288617 A1 | 12/2005 | Yaron et al. |
| 2005/0288619 A1 | 12/2005 | Gharib et al. |
| 2006/0020248 A1 | 1/2006 | Prescott |
| 2006/0032507 A1 | 2/2006 | Tu |
| 2006/0036207 A1 | 2/2006 | Koonmen et al. |
| 2006/0069340 A1 | 3/2006 | Simon |
| 2006/0074375 A1 | 4/2006 | Bergheim et al. |
| 2006/0084907 A1 | 4/2006 | Bergheim et al. |
| 2006/0116626 A1 | 6/2006 | Smedley et al. |
| 2006/0149194 A1 | 7/2006 | Conston et al. |
| 2006/0155238 A1 | 7/2006 | Shields |
| 2006/0173397 A1 | 8/2006 | Tu et al. |
| 2006/0195055 A1 | 8/2006 | Bergheim et al. |
| 2006/0195056 A1 | 8/2006 | Bergheim et al. |
| 2006/0200113 A1 | 9/2006 | Haffner et al. |
| 2006/0235367 A1 | 10/2006 | Takashima et al. |
| 2006/0241749 A1 | 10/2006 | Tu et al. |
| 2006/0276739 A1 | 12/2006 | Brown |
| 2007/0010827 A1 | 1/2007 | Tu et al. |
| 2007/0088242 A1 | 4/2007 | Coroneo |
| 2007/0088432 A1 | 4/2007 | Solovay et al. |
| 2007/0106235 A1 | 5/2007 | Coroneo |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0191863 A1 | 8/2007 | De Juan et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2008/0015488 A1 | 1/2008 | Tu et al. |
| 2008/0045878 A1 | 2/2008 | Bergheim et al. |
| 2008/0195027 A1 | 8/2008 | Coroneo |
| 2008/0200860 A1 | 8/2008 | Tu et al. |
| 2008/0228127 A1 | 9/2008 | Burns et al. |
| 2008/0234624 A2 | 9/2008 | Bergheim et al. |
| 2009/0036819 A1 | 2/2009 | Tu et al. |
| 2009/0138022 A1 | 5/2009 | Tu et al. |
| 2010/0234790 A1 | 9/2010 | Tu et al. |
| 2010/0274259 A1 | 10/2010 | Yaron et al. |

FOREIGN PATENT DOCUMENTS

| | | |
|---|---|---|
| EP | 1310222 A2 | 5/2003 |
| EP | 1473004 A2 | 11/2004 |
| EP | 1477146 A2 | 11/2004 |
| EP | 1418868 B1 | 3/2008 |
| EP | 1977724 A1 | 10/2008 |
| EP | 1545655 B1 | 12/2008 |
| EP | 2027837 A2 | 2/2009 |
| GB | 2101891 A | 1/1983 |
| RU | 2018289 C1 | 8/1994 |
| RU | 2056818 C1 | 3/1996 |
| RU | 2074686 C1 | 3/1997 |
| RU | 2074687 C1 | 3/1997 |
| RU | 2157678 C1 | 10/2000 |
| WO | WO-89/00869 A1 | 2/1989 |
| WO | WO-91/12046 A1 | 8/1991 |
| WO | WO-92/19294 A1 | 11/1992 |
| WO | WO-94/02081 A1 | 2/1994 |
| WO | WO-94/09721 A1 | 5/1994 |
| WO | WO-94/09837 A1 | 5/1994 |
| WO | WO-94/13234 A1 | 6/1994 |
| WO | WO-95/08310 A1 | 3/1995 |
| WO | WO-96/20742 A1 | 7/1996 |
| WO | WO-96/36377 A1 | 11/1996 |
| WO | WO-98/23237 A1 | 6/1998 |
| WO | WO-98/30181 A1 | 7/1998 |
| WO | WO-99/26567 A1 | 6/1999 |
| WO | WO-00/06223 A1 | 2/2000 |
| WO | WO-00/64389 A1 | 11/2000 |
| WO | WO-00/64390 A1 | 11/2000 |
| WO | WO-00/64391 A1 | 11/2000 |
| WO | WO-00/64393 A1 | 11/2000 |
| WO | WO-00/64511 A1 | 11/2000 |
| WO | WO-01/78631 A2 | 10/2001 |
| WO | WO-01/78656 A2 | 10/2001 |
| WO | WO-01/97727 A1 | 12/2001 |
| WO | WO-02/36052 A1 | 5/2002 |
| WO | WO-02/070045 A1 | 9/2002 |
| WO | WO-02/074052 A2 | 9/2002 |
| WO | WO-02/080811 A2 | 10/2002 |
| WO | WO-02/080829 A2 | 10/2002 |
| WO | WO-02/087418 A2 | 11/2002 |

(56) References Cited

FOREIGN PATENT DOCUMENTS

| WO | WO-02/087479 A2 | 11/2002 |
|---|---|---|
| WO | WO-02/089699 A2 | 11/2002 |
| WO | WO-02/102274 A2 | 12/2002 |
| WO | WO-03/015659 A2 | 2/2003 |
| WO | WO-03/015667 A1 | 2/2003 |
| WO | WO-03/041622 A2 | 5/2003 |
| WO | WO-03/073968 A2 | 9/2003 |
| WO | WO-03/099175 A1 | 12/2003 |
| WO | WO-2004/014218 A2 | 2/2004 |
| WO | WO-2004/026347 A2 | 4/2004 |
| WO | WO-2004/043231 A2 | 5/2004 |
| WO | WO-2004/056294 A1 | 7/2004 |
| WO | WO-2004/060219 A1 | 7/2004 |
| WO | WO-2004/062469 A2 | 7/2004 |
| WO | WO-2004/110391 A2 | 12/2004 |
| WO | WO-2005/016418 A1 | 2/2005 |
| WO | WO-2005/046782 A1 | 5/2005 |
| WO | WO-2005/055873 A2 | 6/2005 |
| WO | WO-2005/105197 A2 | 11/2005 |
| WO | WO-2005/107664 A2 | 11/2005 |
| WO | WO-2005/107845 A1 | 11/2005 |
| WO | WO-2006/012421 A2 | 2/2006 |
| WO | WO-2006/036715 A2 | 4/2006 |
| WO | WO-2007/087061 A2 | 8/2007 |
| WO | WO-2007/115259 A2 | 10/2007 |
| WO | WO-2007/130393 A2 | 11/2007 |
| WO | WO-2008/061043 | 5/2008 |

OTHER PUBLICATIONS

Bick MW "Use of tantalum for ocular drainage" Arch Ophthal. 42(4): 373-88 (1949).
Bietti "The present state of the use of plastics in eye surgery" Acta Ophthalmol (Copenh) 33(4):337-70 (1955).
Brown et al., "Internal Sclerectomy for Glaucoma Filtering Surgery with an Automated Trephine," Archives of Ophthalmology, 105:133-136 (1987).
Burchfield JC, Kass MA, Wax MB. Primary valve malfunction of the Krupin eye valve with disk. J Glaucoma. Jun. 1997;6(3):152-6.
Chiou et al. "Ultrasound biomicroscopy of eyes undergoing deep sclerectomy with collagen implant" Br J Ophthalmol 80 (1996), pp. 541-544.
Chylack LT, Bellows AR. Molecular sieving in suprachoroidal fluid formation in man. Invest Ophthalmol Vis Sci 17: 420, 1978.
Classen et al. "A histopathologic and immunohistorchemical analysis of the filtration bleb after unsuccessful glaucoma seton implantation" Am. J. Ophthalmol. 122:205-12 (1996).
Cohen et al. "First day post-operative review following uncomplicated phacoemulsification" Eye 12(4):634-6 (1998).
Collaborative Normal-Tension Study Group. Comparison of glaucomatous progression between untreated patients with normal-tension glaucoma and patients with therapeutically reduced intraocular pressures. Am J Ophthalmol 1998;126:487-97.
Demailly et al. "Non-penetrating deep sclerectomy (NPDS) with or without collagen device (CD) in primary open-angle glaucoma: middle-term retrospective study" International Ophthalmology 20: 131-140, 1997.
Derwent English abstract for EP 1184010, published Mar. 6, 2002 entitled: "Drainage unit for an eye, consists of a hollow line, a distribution member, and a pressure relief valve which only allows water to leave the eye chamber above a certain pressure," Accession Nbr. 12409716 [351].
Dinakaran et al. "Is the first post-operative day review necessary following uncomplicated phacoemulsification surgery?" Eye, 14(3A):364-6 (2000).
Draeger "Chirurgische Maßnahmen bei kongenitalem Glaukom" (Surgical Interventions in Congenital Glaucoma) Klin Monatsbl Augenheilkd 1993; 202(5): 425-427 [Article in German with English summary included].
Einmahl et al. "Evaluation of a novel biomaterial in the suprachoroidal space of the rabbit eye" Invest Ophthalmol Vis Sci. 43:1533-1539 (2002).
Ellis, RA "A Reduction of Intraocular Pressure Using Plastics in Surgery" Am J Ophth. 50; 1960, 733-742.
Emi et al. "Hydrostatic pressure of the suprachoroidal space" Invest. Ophthal. Visual Sci. 30(2):233-238 (1989).
Fanous MM, Cohn RA. *Propionibacterium endophthalmitis* following Molteno tube repositioning. J Glaucoma. Aug. 1997;6(4):201-2.
Fuchs E. "Detachment of the choroid inadvertently during cataract surgery" [German] von Graefes Arch Ophthalmol, 51:199-224 (1900).
Gills et al. "Action of cyclodialysis utilizing an implant studied by manometry in a human eye" Exp Eye Res 1967; 6:75-78.
Gills, "Cyclodialysis Implants in Human Eyes" Am J Ophth 61:1966,841-846.
Gills JP "Cyclodialysis implants" South Med J. 1967 60(7):692-5.
Goldberg "Management of Uncontrolled Glaucoma With the Molteno System" Australian and New Zealand Journal of Ophthalmology 1987; 15: 97-107.
Gordon MO, Kass. MA, for the Ocular Hypertension Treatment Study Group. The Ocular Hypertension Treatment Study. Design and baseline description of the participants. Arch Ophthalmol 1999:573-83.
Grant, W.M. , MD, Further Studies on Facility of Flow Through the Trabecular Meshwork, A.M.A. Archives of Ophthalmololgy, Oct. 1958, vol. 60, pp. 523-533.
Gross et al. "Surgical therapy of chronic glaucoma in aphakia and pseudophakia" Ophthalmology, 95:1195-201 (1988).
Harper SL, Foster CS. Intraocular lens explantation in uveitis. Int Ophthalmol Clin. 2000 Winter; 40(1):107-16.
Harrington "Cataract and Glaucoma. Management of the coexistent conditions and a description of a new operation combining lens extraction with reverse cyclodialysis." Am J Ophthalmol. May 1966;61(5 Pt 2):1134-40.
Heijl A, Leske MC, Bengtsson B, et al for the Early Manifest Glaucoma Trial Group. Reduction of intraocular pressure and glaucoma progression. Results from the Early Manifest Glaucoma Trial. Arch Ophthalmol 2002;120:1268-79.
Heine I. "Cyclodialysis, a new glaucoma operation" [German] Dtsch Med Wochenschr, 31:824-826 (1905).
Hildebrand et al. "Efficacy of anterior chamber decompression in controlling early intraocular pressure spikes after uneventful phacoemulsification" J. Catact Refract Surg., 29:1087-92 (2003).
Hoskins, et al., "Aqueous Humor Outflow", Becker-Shaffer's Diagnosis and Therapy of the Glaucomas, 6th Edition, Chapter 4, pp. 41-66, 1989.
Howorth D J "Feasibility study for a micromachined glaucoma drainage device" Cranfield University School of industrial and manufacturing science MSc Thesis Academic Year 2001-2002 Sep. 13, 2002.
Hylton et al. "Update on prostaglandin analogs" Curr Opin Ophthalmol, 14:65-9 (2003).
Javitt JC, Chiang YP. Preparing for managed competition. Utilization of ambulatory eye care visits to ophthalmologists. Arch Ophthalmol 1993;111:1034-5.
Jay JL, Allan D. The benefit of early trabeculectomy versus conventional management in primary open-angle glaucoma relative to severity of disease. Eye 1989; 3:528-35.
Jordan J. "A Novel Approach to Suprachoroidal Drainage for the Surgical Treatment of Intractable Glaucoma" J. Glaucoma 15:200-205 (2006).
Karlen et al. "Deep sclerectomy with collagen implant: medium term results" Br. J. Ophthalmol, Jan. 1999, 83(1):6-11.
Kass MA, Heuer DK, Higginbotham EJ, et al for the Ocular Hypertension Treatment Study Group. The Ocular HypertensionTreatment Study. A randomized trial determines that topical ocular hypotensive medication delays or prevents the onset of primary open-angle glaucoma. Arch Ophthalmol 2002;120:701-13.
Klemm et al. "Die Ultraschallbiomikroskopie als Kriterium der Funktionsprüfung des suprachorioidalen Spaltes nach kammerwinkelchirurgischen Eingriffen (Ultrasound Biomicroscopic Imaging for Assessment of the Suprachoroidal Cleft after Angle Surgery)" Klinische Monatsblatter für Augenheilkunde 1997; 210: 74-77 [Article in German with English summary included].

(56) References Cited

OTHER PUBLICATIONS

Klemm et al. "Experimental use of space-retaining substances with extended duration: functional and morphological results" Graefes Arch Clin Exp Ophthalmol Sep. 1995; 233(9):592-7.
Kozlov et al. "Nonpenetrating deep sclerectomy with collagen" Eye microsurgery 3:44-46 (1990) [Russian with English translation].
Krejci "Cyclodialysis with hydroxymethyl methacrylate capillary strip (HCS). Animal experiments with a new approach in glaucoma drainage surgery" Ophthalmologica 1972; 164(2):113-21.
Krejci L. "Microdrainage of anterior chamber of eye glaucoma operation using hydron capillary drain." Acta Univ Carol Med Monogr. 1974;(61):1-90.
Kupfer "Studies on intraocular pressure. I. A technique for polyethylene tube implantation into the anterior chamber of the rabbit." Arch Ophthalmol. Apr. 1961;65:565-70.
La Rocca "Gonioplasty in Glaucoma*A Preliminary Report" Br J Ophth 46:1962, 404-415.
Law et al., "Retinal Complications After Aqueous Shunt Surgical Procedures for Glaucoma" Arch Ophthal.; Dec. 1996; vol. 114:1473-1480.
Lee et al. "Aqueous-venous shunt and intraocular pressure. Preliminary report of animal studies." *Investigative Ophthalmology*. vol. 5 No. 1: 59-64. Feb. 1966.
Lee et al. "Magnetic resonance imaging of the aqueous flow in eyes implanted with the trabeculo-suprachoroidal glaucoma seton" Invest. Ophthalmol. Vis. Sci. 33:948 (1992).
Lee KY. Trabeculo-suprachoroidal shunt for treating recalcitrant and secondary glaucoma. Presented at the American Academy of Ophthalmology Annual Meeting, Anaheim, CA, 1991.
Leske MC, Heijl A, Hussein M, et al for the Early Manifest Glaucoma Trial Group. Factors for glaucoma progression and the effect of treatment. The Early Manifest Glaucoma Trial. Arch Ophthalmol Jan. 2003;121:48-56.
Lichter PR, Musch DC, Gillespie BW, et al and the CIGTS Study Group. Interim clinical outcomes in the Collaborative Initial Glaucoma Treatment Study comparing initial treatment randomized to medications or surgery. Ophthalmology 2001;108:1943-53.
Losche W. "Proposals for improvement of cyclodialysis" Klin Monatsblatter Augenheilkd Augenarztl Fortbild 121(6):715-6 (1952) [German].
Marx et al., "Use of the Ganciclovir Implant in the Treatment of Recurrent Cytomegalovirus Retinitis" Arch Ophthal.; Jul. 1996; vol. 114:815-820.
McPherson "Combined Trabeculotomy and Cataract Extraction as a Single Operation" Tr. Am. Ophth. Soc., vol. LXXIV, 1976; 251-260.
Migdal C, Gregory W, Hitchings R. Long term functional outcome after early surgery compared with laser and medicine in open-angle glaucoma. Ophthalmology 1994;101:1651-7.
Miglior S, Zeyen T, Pfeiffer N, et al for the European Glaucoma Prevention Study Group. The European Glaucoma Prevention Study design and baseline description of the participants. Ophthalmology 2002;109:1612-21.
Miki, MD et al., "Intraocular Cannula for Continuous, Chronic Drug Delivery—Histopathic Observations and Function" Arch Ophthal.; May 1985; vol. 103:712-717.
Molteno et al. "Long tube implants in the management of glaucoma" South African Medical Journal, Jun. 26, 1976;50(27):1062-6.
Molteno et al. "The Vicryl tie technique for inserting a draining implant in the treatment of secondary glaucoma." Australian and New Zealand Journal of Ophthalmology 1986; 14: 343-354.
Moses RA "Detachment of ciliary body-anatomical and physical considerations" Investigative Ophthalmology & Visual Science, Assoc. for Research in Vision and Ophthalmology, US, vol. 4, No. 5, Oct. 1, 1965.
Nesterov AP et al. "Surgical stimulation of the uveoscleral outflow. Experimental studies on enucleated human eyes" Acta Opthalmol (Copenh) June; 57(3):409-17 (1979).
Nguyen et al., "Complications of Baerveldt Glaucoma Drainage Implants" Arch Ophthal.; May 1998; vol. 116:571-575.
O'Brien et al. "Cyclodialysis" Arch Ophthal. 1949;42(5):606-619.

Olsen, Timothy W., et al., Cannulation of the Suprachoroidal Space: A Novel Drug Delivery Methodology to the Posterior Segment, American Journal of Ophthalmology, vol. 142, No. 5, Nov. 2006, pp. 777-787.e2.
Ozdamar et al. "Suprachoroidal seton implantation in refractory glaucoma: a novel surgical technique" J. Glaucoma Aug. 2003; 12(4):354-9.
Pinnas G. et al. "Cyclodialysis with teflon tube implants" Am J. Ophthalmol 1969 Nove; 68(5):879-883.
Portney GL, "Silicone elastomer implantation cyclodialysis." Arch Ophthalmol 1973; 89: 10-12.
Pruett et al., "The Fishmouth Phenomenon—II. Wedge Scleral Buckling" Arch Ophthal.; Oct. 1977; vol. 95:1782-1787.
Qadeer "Acrylic Gonio-Subconjunctival Plates in Glaucoma Surgery" Br J Ophthalmol. Jun. 1954; 38(6): 353-356.
Quigley HA, Vitale S. Models of open-angle glaucoma prevalence and incidence in the United States. Invest Ophthalmol Vis Sci 1997; 38:83-91.
Richards et al. "Artificial Drainage Tubes for Glaucoma" Am J Ophth 60:1965,405-408.
Ritch, et al., "Uveoscleral Outflow", The Glaucomas. St. Louis: Mosby, 1996; pp. 337-343.
Rohen, Johannes W., Anatomy of the Aqueous Outflow Channels, Glaucoma, vol. 1, Chapter 14, pp. 277-296, Edited by J.E. Cairns, Grune & Stratton, Harcourt Brace Jovanovich Publishers, 1986.
Rosenberg et al. "Implants in glaucoma surgery" Chapter 88, The Glaucomas, Ritch et al. Eds. 2nd Ed. Mosby St. Louis 1986; p. 1783-1807.
Row H. "Oieration to control Glaucoma: preliminary report" Arch. Ophthal 12:325 (1934).
Rowan, Patrick J., MD, Combined Cyclodialysis and Cataract Surgery, Ophthalmic Surgery and Lasers, Dec. 1998, vol. 29, No. 12, pp. 962-968 (9 pages).
Sampimon "A New Approach to Filtering Glaucoma Surgery" Ophthalmologica (Basel) 151: 1966, 637-644.
Schappert S. Office visits for glaucoma: United States, 1991-92. Advance data from vital and health statistics. vol. 262. Hyattsville, MD: National Center for Health Statistics, 1995.
Shaffer RN, Weiss DI. Concerning cyclodialysis and hypotony. Arch Ophthalmol 68: 25, 1962.
Sommer A, Tielsch JM, Katz J, et al. Racial differences in the cause-specific prevalence of blindness in east Baltimore. N Engl J Med 1991;325:1412-7.
Sourdille et al. "Reticulated hyaluronic acid implant in non-perforating trabecular surgery." J Cataract Refract Surg 25: 332-339. (1999).
Spiegel et al. "Schlemm's Canal Implant: A New Method to Lower Intraocular Pressure in Patients With POAG?" *Ophthalmic Surgery and Lasers*. vol. 30, No. 6: 492-494. Jun. 1999.
Srinivasan et al. "Microbial contamination of the anterior chamber during phacoemulsification" J. Cataract Refract Surg. 28:2173-6 (2002).
Suguro K, Toris CB, Pederson JE. Uveoscleral outflow following cyclodialysis in the monkey eye using a fluorescent tracer. Invest Ophthalmol Vis Sci 1985: 26, 810.
The Advanced Glaucoma Intervention Study (AGIS): 7. The relationship between control of intraocular pressure and visual field deterioration. The AGIS Investigators. Am J Ophthalmol 2000;130:429-40.
The Glaucoma Laser Trial (GLT) and Glaucoma Laser Trial Follow-up Study: 7. Results. Am J Ophthahnol 1995;120:718-31.
The Glaucoma Laser Trial (GLT). 2. Results of argon laser trabeculoplasty versus topical medicines. The Glaucoma Laser Trial Research Group. Ophthalmology 1990;97:1403-13.
Tielsch JM, Sommer A, Katz J, et al. Racial variations in the prevalence of primary open-angle glaucoma. The Baltimore Eye Survey. JAMA 1991;266:369-74.
Toris CB. Extravascular albumin concentration of the uvea. Invest Ophthalmol Vis Sci 1990; 31:43.
Toris et al. "Aqueous humor dynamics in the aging human eye" Am J. Ophthalmol., 127:407-12 (1999).
Toris et al. "Effect of intraocular pressure on uveoscleral outflow following cyclodialysis in the monkey eye." Investigative Ophthalmology & Visual Science. 26 (1985) 1745-1749.

(56) References Cited

OTHER PUBLICATIONS

Troncosco UM "Cyclodialysis with insertion of metal implant in treatment of glaucoma Preliminary report" Arch. Ophthal. 23:270 (1940).
Troncoso, Manuel U., Tantalum implants for inducing hypotny, Am Journal of Ophthalmology, vol. 32(4):499-508 (1949).
Veen et al. "The gonioseton, a surgical treatment for chronic glaucoma" Documenta Ophthalmologica, vol. 75, Nos. 3-4, 365-375. (1990).
Wagner, Justin A., et al., Characterization of Uveoscleral Outflow in Enucleated Porcine Eyes Perfused under Constant Pressure, Invest Ophthalmol Vis Sci., Published in edited form in Sep. 2004, vol. 45, Issue 9, pp. 3203-3206.
Yablonski, "Some thoughts on the pressure dependence of uveoscleral flow" Journal of Glaucoma, 12(1):90-92 (2003).
Yablonski, "Trabeculectomy with Internal Tube Shunt: a novel glaucoma surgery" J. Glaucoma 14:91-97 (2005).
Coote. "Glaucoma Hollow Fiber Filters—A New Glaucoma Seton. Preliminary Results." *J. Glaucoma.* vol. 8 No. 1 Supplement (1999):p. S4.
Cullen, et al. "Anterior Chamber of Frontal Sinus Shunt for the Diversion of Aqueous Humor: A Pilot Study in Four Normal Dogs". *Veterinary Ophthalmology.* vol. 1. No. 1. (1998):31-39.
Odrich. "The New Technique During Complex Tube-Shunt Implantation". *J. Glaucoma.* vol. 9 No. 3 (2000):278-279.

INTERNAL SHUNT AND METHOD FOR TREATING GLAUCOMA

RELATED APPLICATIONS

This application is a continuation of co-pending U.S. patent application Ser. No. 12/711,201, filed Feb. 23, 2010, entitled "Internal shunt and method for treating glaucoma," which is a continuation of Ser. No. 11/509,327, filed Aug. 23, 2006, entitled "Internal shunt and method for treating glaucoma," which in turn is a continuation of U.S. patent application Ser. No. 10/429,336, filed May 5, 2003. The subject matter of each of the above-noted applications is incorporated by reference in their entirety by reference thereto.

FIELD OF THE INVENTION

This invention pertains to a surgical treatment for glaucoma and, more particularly, to a new method and apparatus for surgically alleviating the intraocular pressure causing the glaucoma condition.

BACKGROUND

Glaucoma is an eye condition in which the hydrostatic pressure within the eye is abnormally high, thereby resulting in damage to the optic nerve. There are many treatments for the glaucoma condition that involve lowering the intraocular pressure, either by means of medication or surgery.

Medicinal treatments either decrease the rate at which aqueous humor is pumped into the eye or improve the outflow of aqueous humor from the eye.

There are three primary surgical methods for treating glaucoma. Presently, none of them are a complete answer to the problem:

a) Cyclodestructive procedures damage the ciliary body of the eye and decrease the rate of aqueous humor production. The main problem is the extremely fine dividing line between too little and too much treatment. This treatment often does not work, or it works too well. When the surgery works too well, a hypotonous eye may develop in which the pressure is too low for normal ocular function and health.

b) Laser therapy of the trabecular meshwork is used to decrease the resistance of outflow of aqueous humor into the Canal of Schlemm. The main problem with this procedure is that it only provides relief for about five years. Re-treatment is often unsuccessful because it may cause too much scarring of the outflow channels. Thus, this procedure can do more harm than good.

c) Shunting of aqueous humor from the anterior chamber through the sclera to outside of the confines of the eye is the most common surgical procedure. Among the shunting procedures, the often-performed trabeculectomy is a type of filtering method. It allows aqueous humor to "filter" out of the eye. A channel is created from the anterior chamber under a scleral flap to the episcleral space. The main problem with this procedure is that the outcome depends on the individual healing properties of the eye in the post-operative period. Trabeculectomy is often much less successful in highly pigmented eyes and eyes with previous surgery, rubeosis, or chronic uveitis. To overcome this problem, several shunts have been devised to carry aqueous humor from the anterior chamber to the episcleral space. Scarring often occurs surrounding the exterior end when shunts are used. This renders the outcome unpredictable.

Another problem with these types of surgical procedures is that the globe is left with a transcleral fistula. The fistula renders the eye susceptible to the ingress of organisms and intraocular infection. This condition is known as endophthalmitis and can be devastating to the eye, since the eye is not naturally designed to defend against this type of onslaught.

The invention seeks to provide a surgical treatment and apparatus that will overcome the many problems associated with present-day surgical procedures.

The current invention provides an indwelling shunt that diverts aqueous humor from the anterior chamber to the blood flowing in the choroidal and uveal tissues. This decreases the intraocular pressure of the glaucomatous eye. The indwelling shunt maintains the area of exposure of aqueous humor with the uvea by physically preventing scarring of the surrounding tissues. The method utilizes the normally occurring 25 mm Hg driving force of the protein colloid osmotic pressure of the blood to maximize the flow of aqueous humor out of the eye (Yablonski, M. E., J of Glaucoma, February 2003, 12(1):90-92).

One of the many problems that this inventive procedure overcomes is the normally low outflow of aqueous humor into the uveal blood caused by the normally low hydraulic permeability between the aqueous humor of the anterior chamber and the uveal blood vessels (Yablonski, ibid.). The internal tube shunt of this invention, however, greatly increases the hydraulic permeability between the aqueous humor and the uveal blood vessels, thus greatly increasing the magnitude of the outflow via this route.

The present invention overcomes the two main objections of most of the current surgical approaches: (a) it requires no permanent transcleral route for the egress of aqueous humor from the eye, and (b) the success of the procedure is not as dependent on the individual healing properties of the eye as it is in other procedures. Therefore, the inventive technique not only works in younger eyes, but it also works in eyes of darkly pigmented individuals, and eyes of patients who have had previous surgery. In addition, the inventive procedure leaves no transcleral route in the eye, thus decreasing the susceptibility to endophthalmitis.

In an article by Stegmann (1990), a procedure is described wherein a non-penetrating deep sclerectomy is performed. The procedure was called "viscocanalostomy" because a viscoelastic substance was injected into the cut ends of the canal of Schlemm after the canal was exposed. Like the present technique, Stegmann first created a thin scleral flap, then created a deep sclerectomy by removing the deep sclera, leaving only a thin layer of sclera of 50 to 100 microns in thickness overlying the choroidal tissue beneath.

It should be observed that Stegmann sutured the overlying scleral flap very tightly, thereby eliminating a final transcleral route for aqueous humor drainage. This implied that the intended mechanism for aqueous humor egress was an intraocular shunt. The mechanism of action of the procedure was proposed by Stegmann to be the access of aqueous humor to the newly dilated canal of Schlemm, from which it flowed from the eye by the usual outflow routes. However, if this were the case, the outflow facility of the eyes should be increased, as measured by tonography. No studies have shown an increase in outflow facility after the viscocanalostomy is performed, despite a marked decrease in intraocular pressure.

Another related technique to that of the current invention is the procedure that sutures a collagen implant beneath the scleral flap into the bed of the deep sclerectomy (M. E. Karlen, E. Sanchez, C. C. Schnyder, M. Sickenberg, and A. Mermoud, Deep sclerectomy with collagen implant: medium term results, Br J Ophthalmol, January 1999, 83(1):6-11). The method provides a non-penetrating deep sclerectomy wherein a collagen implant is placed between the overlying scleral flap and the underlying suprachoroidal space. No dilation of the canal of Schlemm is performed. No flow of aqueous humor into the uveal blood is suggested, and only two scleral flap sutures are used, which renders the scleral flap permeable to transcleral flow and creates a transcleral fistula.

In U.S. Pat. No. 6,383,219, issued on May 7, 2002 to Telandro et al., a related non-penetrating deep sclerectomy is illustrated. The method uses an implant made of a cross-linked hydraluronic acid material, which is shaped like a polyhedron having at least five faces. The material is placed between the overlying scleral flap and the underlying suprachoroidal scleral bed. Unlike the current inventive method, this procedure does not propose that the aqueous humor flows mainly into the adjacent uveal blood in response to its protein colloid osmotic pressure. The use of only two sutures in the overlying scleral flap renders this flap permeable to transcleral flow, creating a transcleral fistula.

The stated mechanism for relief in Telandro et al. is the high water content that acts like a wick, i.e., it transports the ocular fluids by capillary action. No mention is made of flow of aqueous humor into the uveal blood, and it is implied that the final destination of the flow of aqueous humor is across the overlying scleral flap into the episcleral space. This method is similar to a conventional trabeculectomy and other filtering procedures.

Some internal shunts have previously been proposed. In U.S. Pat. No. 6,450,984, issued to Lynch and Brown on Sep. 17, 2002, a shunt is illustrated that shunts fluid from the anterior chamber. The shunt is placed under a scleral flap and into the open ends of the canal of Schlemm. This method requires normal drainage of aqueous humor from the canal of Schlemm into the episcleral veins. Since in open angle glaucoma, which is the most common type of glaucoma, flow through the canal of Schlemm is impaired, this technique appears flawed. To the best of knowledge and belief, no reports exist in the literature depicting the successful implementation of this technique.

In U.S. Pat. No. 5,601,094, issued on Feb. 11, 1997 to Reiss, a shunt is described which causes flow of aqueous humor from the anterior chamber to the suprachoroidal space. Unlike the present invention, however, the shunt is exteriorized before it enters the suprachoroidal space. This renders the eye susceptible to endopthalmitis. To the best of knowledge and belief, there have been no successful reports for this technique in the literature.

In U.S. Pat. No. 4,521,210, issued on Jun. 4, 1985 to Wong, a shunt is illustrated that extends from the anterior chamber to the suprachoroidal space. The shunt is designed to create a permanent cyclodialysis cleft and shunt aqueous fluid to the suprachoroidal space from the anterior chamber. The suprachoroidal space is surgically entered and the ciliary body disinserted from the scleral spur. To the best of knowledge and belief, there have not been any reports in the literature of the success of this technique.

SUMMARY

In accordance with the present invention, a surgical technique and apparatus are illustrated for alleviating the glaucoma condition. The current invention provides an indwelling shunt that diverts aqueous humor from the anterior chamber to the blood flowing in the choroidal and uveal tissues. This decreases the intra-ocular pressure. The indwelling shunt maintains the area of exposure of aqueous humor with the uvea by physically preventing scarring of the surrounding tissues. The method utilizes the 25 mm Hg driving force of the protein colloidal osmotic pressure of the blood to maximize the flow.

One method illustrated in FIGS. 1, 3, and 4 comprises the initial step of folding back a one-third scleral thickness scleral flap hinged at the peripheral cornea. A small cavity is generated, extending into the peripheral cornea, by the removal of deep scleral tissue (known as a deep sclerectomy), leaving a very thin, approximately 50 micron in thickness scleral bed (FIG. 4) over the underlying choroid. The suprachoroidal space is entered at the lateral edges of the scleral bed by cutting directly or at a laterally slanted angle. The shunt, which can comprise a precut tube with polished edges, is placed one end permanently into the suprachoroidal space and the other in the scleral lake and is sutured into the overlying sclera. The precut tube can be delivered with a suture in place for ease of deployment. Other examples of structures that can function as a shunt in addition to a hollow tube include a solid section of material grooved to carry aqueous humor, or a structure of open cell foam or other porous material, and similar structures in each case made from biologically compatible materials.

After suturing, one end of the tube is in the suprachoroidal space and the other is in the scleral lake created by the deep sclerectomy. Then a trabeculectomy specimen is created, plus a peripheral iridectomy, as in a standard trabeculectomy. The scleral flap is turned back to its normal position resting on the deep scleral shelf and is sutured to the adjacent sclera with six to ten interrupted sutures to yield a tight closure. The shunt can be fabricated from silicone or other biocompatible materials. One or two such tubes can be placed on each lateral side of the deep sclerectomy. These tubes not only shunt aqueous humor from the scleral lake into the suprachoroidal space, they also help maintain the volume of the scleral lake by acting as a physical barrier between the overlying scleral flap and the underlying scleral bed.

In another version of this procedure (FIG. 2), the scleral lake is smaller and is separated from the anterior chamber by an approximately 3 mm wide layer of full thickness sclera. A tunnel is created with a 23 gauge needle and one end of the tube is inserted through the tunnel into the anterior chamber. The other end of the tube is placed through an incision, at the posterior edge of the scleral bed, into the posterior suprachoroidal space where it is sutured to the overlying sclera. Then the scleral flap is tightly sutured back into place. Other examples of structures that can function as a shunt in addition to a hollow tube include a solid section of material grooved to carry aqueous humor, or a structure of open cell foam or other porous material, and similar structures in each case made from biologically compatible materials.

It is an object of this invention to provide an improved surgical technique and apparatus for treating glaucoma.

It is another object of the present invention to provide both a surgical method and an apparatus that utilizes the uveal blood vessels to drain aqueous humor from the anterior chamber of the eye to decrease intra-ocular pressure in the treatment of glaucoma.

BRIEF DESCRIPTION OF THE DRAWINGS

A complete understanding of the present invention may be obtained by reference to the accompanying drawings, when considered in conjunction with the subsequent detailed description, in which.

Figure 1:
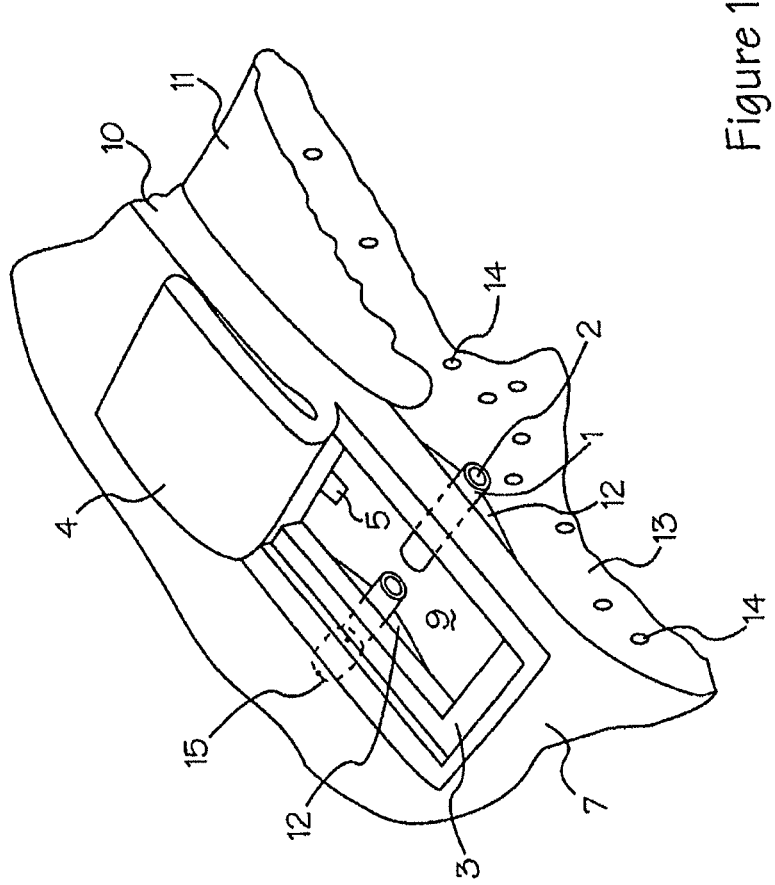
FIG. 1 illustrates a top, three-dimensional, perspective, enlarged view of a portion of the eye, shown in partial cutaway.

For purposes of brevity and clarity, like components and elements of the apparatus of this invention will bear the same designations or numbering throughout the FIGURES.

DETAILED DESCRIPTION

Generally speaking, a surgical technique and apparatus is described wherein an indwelling shunt is placed in the eye of patients having glaucoma. The shunt diverts aqueous humor from the anterior chamber to the suprachoroidal space from which it is removed by the blood flowing in the choroidal and uveal tissues. This decreases the intra-ocular pressure. The indwelling shunt maintains the area of exposure of aqueous humor with the uvea by physically preventing scarring of the surrounding tissues. The method utilizes the 25 mm Hg driving force of the protein colloidal osmotic pressure of the blood to drive aqueous humor into the blood.

In FIGS. 1 through 4, a portion of an eye is shown being surgically prepared with a hollow tube (indwelling shunt) 1 for the treatment of glaucoma. The hollow tube 1 has an interior open space 2 in which fluid (not shown) is transferred. The tube 1 diverts aqueous humor from the scleral lake 8 (FIG. 4) to the suprachoroidal space 12, as best observed with reference to FIGS. 1 and 3. This shunting of the aqueous humor decreases the intra-ocular pressure. The indwelling shunt 1 maintains the area of exposure of aqueous humor with the uvea by physically preventing scarring of the surrounding tissues. The method utilizes the 25 mm Hg driving force of the protein colloidal osmotic pressure of the blood of the uveal blood vessels 14 to maximize the flow (Yablonski, ibid.).

Figure 2:
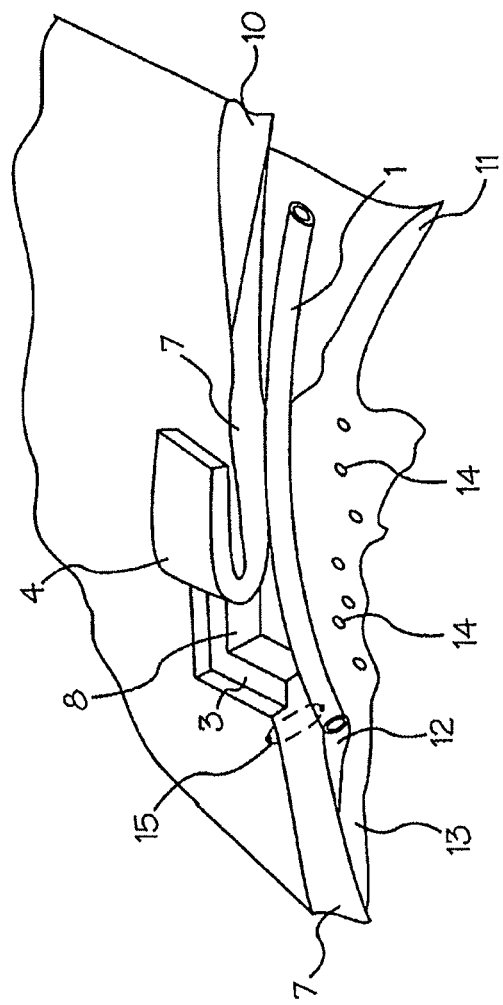
FIG. 2 depicts a top, three-dimensional perspective view of the second type of internal tube shunt procedure, enlarged view of the portion of the eye, shown in partial cutaway.

The method comprises the initial step of folding back the scleral flap 4 of the eye (FIG. 1). A small cavity, the deep scleral lake 8, is generated by the removal of tissue in the sclera 7. The suprachoroidal space 12, a normally occurring potential space, is entered by cutting directly, or at a slanted angle through the scleral bed 9. The shunt 1, which can comprise a precut tube with polished edges, is then inserted into the suprachoroidal space 12 and sutured by sutures 15 to the overlying sclera 7 therein, as best seen in FIGS. 1 and 2. The precut tube 1 can also contain sutures fabricated in place for ease of deployment.

Figure 4:
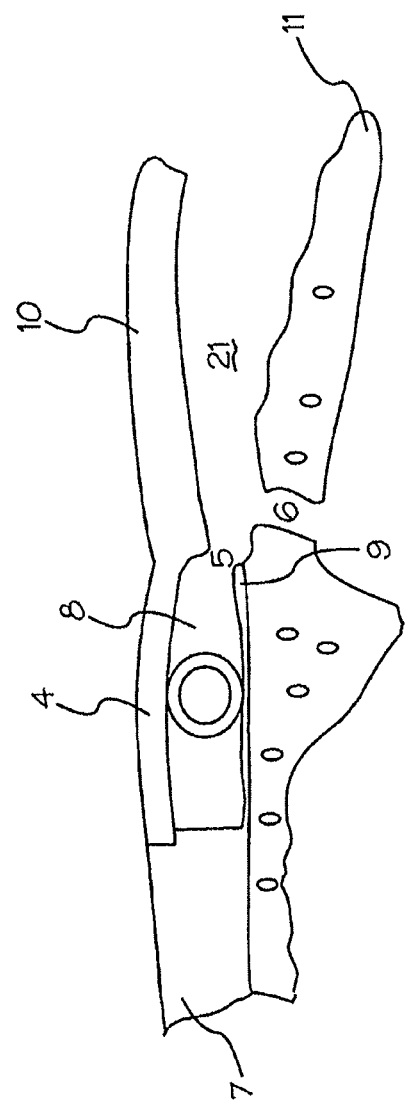
FIG. 4 illustrates a sectional view of the portion of the eye depicted in FIGS. 1 and 3.

After suturing the tube 1 in place, a trabeculectomy specimen 5 may be removed, thus creating a direct communication to the anterior chamber 21 (best seen in FIG. 4). A peripheral iridectomy 6 may be created in the iris 11. The scleral flap 4 is then replaced, resting on the deep scleral shelf 3 where it is tightly sutured to the adjacent sclera 7. The shunt 1 can be fabricated from silicone or other biocompatible materials. It can be seen, therefore, that this technique does not create a permanent cyclodialysis cleft and does not disinsert the ciliary body from the scleral spur.

Referring to FIG. 1, the internal tube shunt 1 of the present invention is inserted and sutured between the suprachoroidal space 12 and the deep scleral lake 8 generated by the surgical forming of a scleral flap 4, and a deep sclerectomy starting 4.5 mm from the limbus and extending into the peripheral cornea 10. Since the deep sclerectomy is about 1 mm smaller than the dimensions of the scleral flap 4, a deep scleral ledge 3 approximately 0.5 mm in width is created on the lateral and posterior aspect of the deep scleral lake 8.

Referring now to FIG. 2, the shunt 1 of the present invention is illustrated passing from the anterior chamber 21 through the adjacent sclera 7, through a posterior deep scleral lake 8, and into the posterior suprachoroidal space 12 where it is sutured to the overlying sclera 7. The deep scleral lake 8 is generated by forming a scleral flap 4 and deep sclerectomy similar to that of FIG. 1 but with an anterior end 3 mm posterior to the cornea 10.

Figure 3:
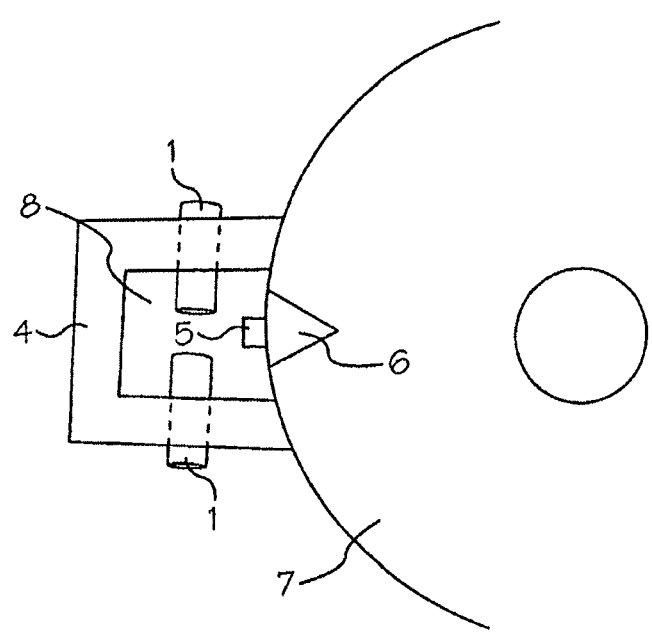
FIG. 3 shows a top view of the portion of the eye illustrated in FIG. 1.

Referring now to FIG. 3, the shunt 1 of the present invention is inserted and laterally sutured into the suprachoroidal space 12 on each side of the deep scleral lake 8 generated by forming a scleral flap 4 and a deep sclerectomy, with the scleral flap 4 sutured back into place over the ends of the tube shunts 1. Also shown are the peripheral iridectomy 6 and the trabeculectomy site 5.

Referring to FIG. 4, the shunt of this invention is seen in the deep scleral lake 8 between the overlying scleral flap 4 and the underlying scleral bed 9. Also shown are the trabeculectomy site 5 and the peripheral iridectomy 6.

FIGS. 1, 3, and 4 show one possible incorporation of the invention where aqueous humor gains access to the shunt 1 via a trabeculectomy 5 between the anterior chamber 21 and the deep scleral lake 8 where one end of the tube 1 lies. From the deep scleral lake 8, aqueous humor is shunted via the tube 1 to the suprachoroidal space 12.

FIG. 2 shows another possible incorporation of the invention in which aqueous humor is shunted directly by a tube 1 that passes from the anterior chamber 21 through the sclera 7 between the anterior chamber 21 and the deep sclerectomy space, and into the suprachoroidal space 12 at the posterior aspect of the deep sclerectomy where it is sutured to the overlying sclera 7.

In this version, the deep sclerectomy is smaller than the deep scleral lake 8 shown in FIGS. 1 and 4. Unlike the version in FIGS. 1 and 4 where the deep scleral lake 8 serves as the pool of aqueous humor which flows into the tube 1, in the version of FIG. 2, the deep sclerectomy serves only to allow the surgeon access for insertion of the tube 1 into the anterior chamber 21, anteriorly, and the suprachoroidal space 12, posteriorly. After the tube 1 is in place, the scleral flap 4 is sutured to the adjacent sclera 7 and no permanent deep scleral lake 8 need persist.

Since other modifications and changes varied to fit particular operating requirements and environments will be apparent to those skilled in the art; the invention is not considered limited to the examples chosen for purposes of disclosure and covers all changes and modifications which do not constitute departures from the true spirit and scope of this invention.

Having thus described the invention, what is desired to be protected by Letters Patent is presented in the subsequently appended claims.

What is claimed is:

1. A method of treating glaucoma, comprising:
providing an elongated tube comprising a first end having at least one inflow port, at least one outflow port and an internal fluid passageway communicating between the at least one inflow port and at least one outflow port;
creating a passageway in eye tissue;
inserting the tube through the passageway;
positioning the tube within an interior of the eye such that the at least one inflow port of the tube is positioned in and communicates with the anterior chamber and the at least one outflow port of the tube communicates with the suprachoroidal space, and such that a portion of the tube having the first end bends away from an inner surface of the cornea;
leaving only the tube inside the eye; and diverting aqueous humor through the fluid passageway from the anterior chamber toward the suprachoroidal space.

2. The method of claim 1, wherein the tube comprises a rounded, outer surface that contacts a portion of the sclera.

3. The method of claim 1, further comprising attaching a retaining structure to an end of the tube.

4. The method of claim 3, wherein the retaining structure comprises a suture attached to a distal end of the tube.

5. The method of claim 1, further comprising cutting the tube prior to implantation.

6. The method of claim 1, wherein the passageway is created using a needle.

7. The method of claim 1, wherein the at least one outflow port is positioned in the suprachoroidal space.

8. The method of claim 1, wherein the tube is cylindrical.

9. The method of claim 1, wherein aqueous humor flows directly into the suprachoroidal space via the fluid passageway.

10. A method of treating glaucoma, comprising:
   providing a tube having an internal lumen, a first end with a first opening for fluid to flow into the internal lumen, and a second opening for fluid to flow out of the internal lumen;
   creating a passageway in eye tissue;
   inserting the tube through the passageway;
   positioning the tube inside an eye so that the first opening is inside the anterior chamber and the second opening communicates with the suprachoroidal space and such that that a portion of the tube having the first end bends away from an inner surface of the cornea;
   leaving only the tube inside the eye; and
   causing fluid to flow from the anterior chamber into the internal lumen through the first opening and out of the internal lumen toward the suprachoroidal space through the second opening.

11. The method of claim 1 wherein the tube comprises a rounded, outer surface that contacts a portion of the sclera.

12. The method of claim 10, wherein the passageway is created using a needle.

13. The method of claim 10, wherein the second opening is positioned in the suprachoroidal space.

14. The method of claim 10, wherein the tube is cylindrical.

15. The method of claim 10, wherein aqueous humor flows directly into the suprachoroidal space via the internal lumen.

* * * * *